United States Patent
Czechowski et al.

(10) Patent No.: US 8,679,803 B2
(45) Date of Patent: Mar. 25, 2014

(54) GLUCOSE CONVERSION TO ETHANOL VIA YEAST CULTURES AND BICARBONATE IONS

(75) Inventors: Melvin H. Czechowski, Doylestown, PA (US); Steven A. Bolkan, Hopewell, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 13/096,175

(22) Filed: Apr. 28, 2011

(65) Prior Publication Data

US 2011/0201093 A1  Aug. 18, 2011

Related U.S. Application Data

(62) Division of application No. 12/006,136, filed on Dec. 31, 2007, now Pat. No. 7,960,153.

(51) Int. Cl.
*C12P 7/06* (2006.01)

(52) U.S. Cl.
USPC ............ 435/161; 435/105; 435/171; 435/162

(58) Field of Classification Search
USPC .......................................... 435/161
See application file for complete search history.

(56) References Cited

U.S. PATENT DOCUMENTS

| | | | |
|---|---|---|---|
| 4,581,235 A * | 4/1986 | Cooley et al. ................... | 426/11 |
| 4,822,737 A | 4/1989 | Saida | |
| 4,910,144 A | 3/1990 | Saito et al. | |
| 5,231,017 A | 7/1993 | Lantero et al. | |
| 5,266,337 A | 11/1993 | Barwald et al. | |
| 6,284,453 B1 | 9/2001 | Siano | |
| 6,451,567 B1 | 9/2002 | Barclay | |
| 6,475,759 B1 | 11/2002 | Carlson et al. | |
| 6,555,350 B2 * | 4/2003 | Ahring et al. ................... | 435/162 |
| 7,011,969 B2 * | 3/2006 | Yoneda et al. ........... | 435/252.31 |
| 7,078,201 B2 | 7/2006 | Burmaster | |
| 7,285,402 B2 | 10/2007 | Gaddy et al. | |
| 2003/0129715 A1 | 7/2003 | Carlson et al. | |
| 2005/0272134 A1 | 12/2005 | Hughes | |
| 2007/0190627 A1 | 8/2007 | Henderson et al. | |
| 2008/0138872 A1 * | 6/2008 | Smith et al. ................... | 435/165 |
| 2010/0216201 A1 * | 8/2010 | Soong et al. ................... | 435/161 |

OTHER PUBLICATIONS

Frick et al., Indirect method for characterization of carbon dioxide levels in fermentation broth, Journal of Bioscience and Bioengineering, vol. 87, p. 344-351, 1999.*

Sedlak et al., Proudction of ethanol from cellulosic biomass hydrolysated using genetically engineered *Saccharomyces* yeast capable of cofermenting glucose and xylose, Applied biochemistry and biotechnology, vol. 113-116, p. 403-416, 2004.*

* cited by examiner

*Primary Examiner* — Jon P Weber
*Assistant Examiner* — Tiffany Gough
(74) *Attorney, Agent, or Firm* — Fishman & Associates, LLC.

(57) ABSTRACT

The present invention is directed to the enhanced production of ethanol from fermentation using an ethanol producing microorganism. In particular, the present invention provides a process for the enhanced growth and metabolism of an ethanol producing microorganism (e.g., yeast), for the purpose of increasing or enhancing ethanol production, both in terms of total ethanol produced and in terms of the time required for ethanol producing microorganisms to convert carbohydrates and/or sugars to end products (i.e., ethanol). In accordance with this invention bicarbonate ions are used to enhance ethanol fermentation and/or reduce the time required for ethanol producing microorganisms to convert carbohydrates and/or sugars to end products, i.e., ethanol. The present invention can also be used for enhancing fermentation end products in, for example, the fuel ethanol, industrial, cheese, brewing, and wine making industries.

5 Claims, 1 Drawing Sheet

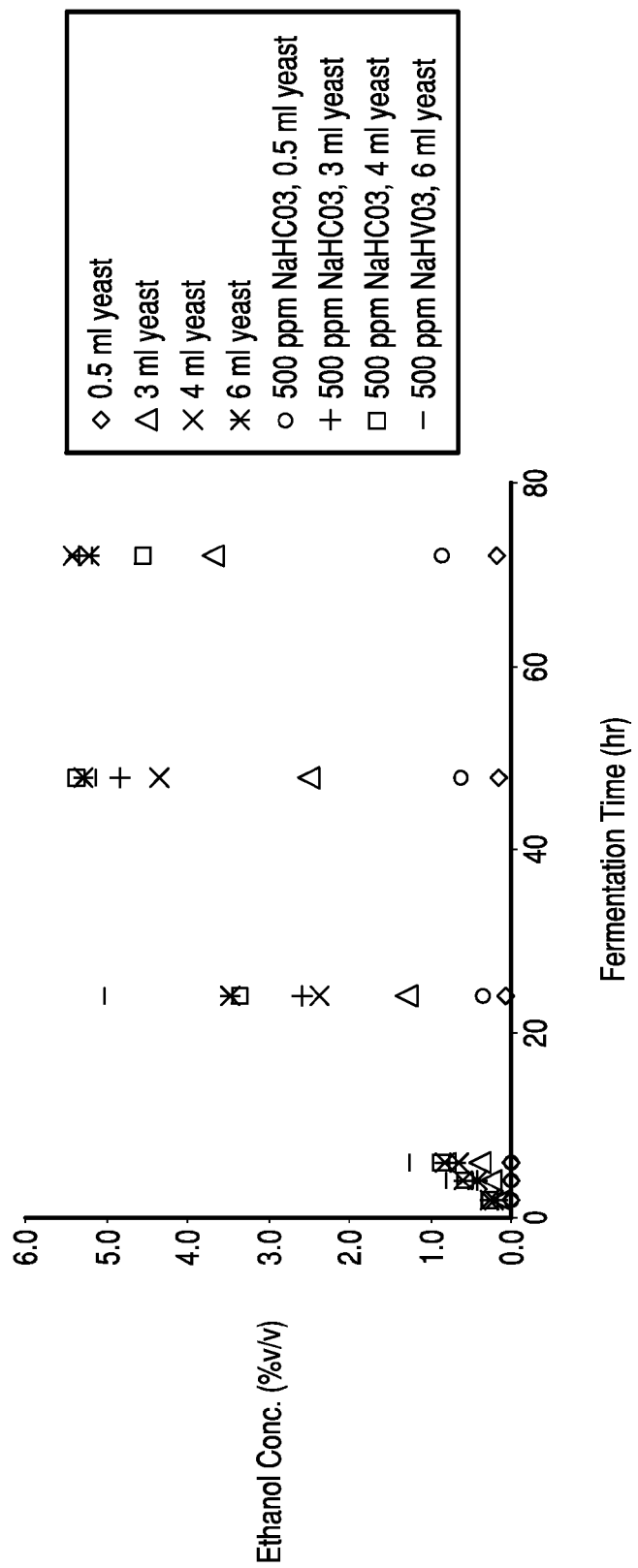

GLUCOSE CONVERSION TO ETHANOL VIA YEAST CULTURES AND BICARBONATE IONS

CROSS-REFERENCE TO RELATED APPLICATIONS

The present application is a division of U.S. patent application Ser. No. 12/006,136, filed Dec. 31, 2007, the disclosure of which is incorporated herein by reference in its entirety.

FIELD OF THE INVENTION

The present invention is directed to a process for the production of ethanol by fermentation. More specifically, the present invention is directed to a process to improve ethanol yield, and decrease fermentation time.

BACKGROUND OF THE INVENTION

The production of alcoholic beverages by the fermentation of fruit and grains is of ancient origin. In more recent times, the isolation of ethanol in concentrated or in pure form for use either in beverages, in industry, or as fuel, has assumed considerable importance. In general, ethanol may be produced by the fermentation of simple sugars such as glucose and fructose and oligosaccharides such as sucrose. Such substances and mixtures thereof which, without prior chemical modification, are convertible to ethanol will be referred to herein as "fermentable carbohydrates." More complex carbohydrates such as starches and cellulosic materials also may be converted to ethanol by fermentation, but usually only after they are degraded to lower molecular weight sugars or related materials. The fermentation proceeds in an anaerobic environment, with production of carbon dioxide by-product. The Kirk-Othmer Encyclopedia of Chemical Technology, Third Edition, John Wiley and Sons, New York, N.Y., presents a condensed summary of the state of the art of producing and isolating fermentation-ethanol in Volume 9, at pages 352-361, which is incorporated herein by reference.

Ethanol has widespread application as an industrial chemical, gasoline additive or straight liquid fuel. As a fuel or fuel additive, ethanol dramatically reduces air emissions while improving engine performance. As a renewable fuel, ethanol reduces national dependence on finite and largely foreign fossil fuel sources while decreasing the net accumulation of carbon dioxide in the atmosphere.

In contrast to energy production by combustion of fossil fuels, energy production by combustion of contemporary biomass (predominantly in the form of harvested plant material) or fuels derived from such biomass is regarded as being "$CO_2$-neutral", since the amount of $CO_2$ released by combustion of a given amount of such biomass corresponds to the amount of $CO_2$ which was originally taken up from the atmosphere during the build-up of that amount of biomass.

Among fuels derived from plant biomass, ethanol has received particular attention as a potential replacement for or supplement to petroleum-derived liquid hydrocarbon products. To minimize the production cost of ethanol produced from biomass (also referred to in the following as "bioethanol") it is important to use biomass in the form of low-cost by-products from gardening, agriculture, forestry, the timber industry and the like; thus, for example, materials such as straw, maize stems, forestry waste (log slash, bark, small branches, twigs and the like), sawdust and wood-chips are all materials which can be employed to produce bioethanol.

Biomass typically includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables are usually consumed as food. Conversely, biomass high in cellulose, hemicellulose and lignin are not readily digestible and are primarily utilized for wood and paper products, fuel, or are disposed of.

Biomass contains two basic constituents, carbohydrates and lignin. The carbohydrate content of the biomass contains cellulose and hemicellulose. Both cellulose and hemicellulose can be converted to sugars of glucose and xylose. Fermentation converts glucose and xylose to ethanol using enzymes produced by microorganisms, for example, as shown in U.S. Pat. No. 5,789,210. Control of nutrients, pH, temperature, sugar concentration, and microorganism concentration all affect rate of fermentation to form ethanol. When ethanol concentration reaches above about 6 to 12%, ethanol concentration can be lethal to the microorganisms employed for fermentation. To reduce ethanol concentration within broth employed for fermentation and maintain activity of microorganisms, extraction of ethanol from the broth by solvents non-toxic to microorganisms, as disclosed in U.S. Pat. Nos. 5,110,319, 4,865,973 and No. 4,517,298. The operations disclosed require energy for vaporization of ethanol and subsequent condensation to produce liquid ethanol.

The various operations in processes for obtaining ethanol from such recurring sources as cellulose, cane sugar, amylaceous gains and tubers, e.g., the separation of starch granules from non-carbohydrate plant matter and other extraneous substances, the acid and/or enzymatic hydrolysis of starch and/or cellulose to fermentable sugar (saccharification), the fermentation of sugar to a dilute solution of ethanol and the recovery of anhydrous ethanol by distillation, have been modified in numerous ways to achieve improvements in product yield, production rates and so forth. For ethanol to realize its vast potential as a partial or total substitute for petroleum fuels or as a substitute chemical feedstock, it is necessary that the manufacturing process be as efficient in the use of energy and raw materials as possible so as to maximize the energy return for the amount of ethanol produced and enhance the standing of the ethanol as an economically viable replacement for petroleum-based chemicals. To date, however, relatively little concern has been given to the energy requirements for manufacturing ethanol from biomass and consequently, little effort has been made to minimize the thermal expenditure for carrying out any of the discrete operations involved in the manufacture of ethanol from vegetative sources.

There are three basic methods known for accelerating the fermentation rates of a sugar media to ethanol. These methods include 1) increasing the cell density, and/or 2) reducing the concentration of inhibitory compound(s) (with ethanol being most inhibitory due to its osmolality and toxic effects) in the media as suggested by Dale in prior U.S. Pat. Nos. 4,665,027 and 5,141,861. The third method is to control the growth environment; such as with trace elements, vitamins, amino acid, pH, and temperature (Biology of Microorganisms, $7^{th}$ edition, Brock, Madigan, Martinko and Parler. Prenitice Hall, New Jersey 1994). During a normal batch ethanol fermentation with standard S. cerevisae strains, a final cell concentration of between 1.5 and 15 g/l cells is achieved. It is often noted that cell growth completely stops after a certain cell density is reached (Holzberg et al, 1967). The oxygen tension in the fermentation is important in these batch fermentations, as the cells will convert a larger fraction of the sugar substrate towards cell mass production as the amount of oxygen available to the cells increases. Trace oxygen can serve as a nutrient during the anaerobic fermentation of sugars, allowing more cell production that results in a greater fermentation rate of sugar to ethanol. Cysewski and Wilke (1978) show an optimal oxygen tension of about 0.1 mm $O_2$. To maintain a cell density higher than the natural maximum attained in the fermenter, methods for keeping the cells in the fermenter must be utilized. A high cell density can be maintained either by recycling cells (through membrane or centrifugal techniques) or by retaining or immobilizing the cells within the reactor. Immobilization would seem to be advantageous as the capital expense of a cell recovery and recycle system can be eliminated. There has been a good deal of work over the last 10-15 years on immobilizing organisms to maintain a high cell density in the bioreactor. Immobilization can take one of several approaches, 1) entrapment within a gel bead or plate, 2) adsorption onto a solid matrix, or 3) self-agglomeration or flocculation into flakes or pellets.

Increasing temperature generally speeds a fermentation until the temperature becomes high enough to cause cell death. Fermentation rates are generally noted to increase from 20° to 32° C., doubling with a 5° C. increase in temperature.

The traditional process of fermentation is carried out in a conventional batch operation utilizing yeast as the fermenting organism. To increase the efficiency a variation of the batch operation occasionally includes recycling of the yeast cells by systems such as sedimentation, centrifugation, or ultrafiltration. Normally this batch operation is conducted in two stages. The first stage involves propagation of the yeast and is referred to as the growth stage. The second stage involves the anaerobic process of ethanol production which is accompanied by a depletion of the oxygen. Further propagation of the yeast occurs during the anaerobic process of ethanol production.

Typically, a yeast inoculum is prepared in stage one. The requirements for maximum yeast reproduction are adequate amounts of carbon, nitrogen, minerals and oxygen, a pH in the range of 3.5 to 4.5, and a temperature in the range of 29°-35° C. Aerobic growth conditions define a system for more efficient production of yeast but under which no ethanol is produced. Stage two is the fermentation stage where the alcohol is actually produced by the yeast from the fermentable sugars. The yeast inoculum produced in stage one is used to seed a large fermenter containing glucose at appropriate pH, temperature and sugar concentration. Glucose was formed from the conversion of dextrins via saccharification enzymes. The dextrins were derived from molasses, corn starch materials, etc. via liquification enzymes. The inoculation rate can be 5 to 10 million cells per ml and during the fermentation the viable cell count can increase to 150-200 million cells per ml. Heat produced is controlled through the use of cooling coils. At these yeast levels, a final ethanol concentration of about 9 to 11% (v/v) can be obtained in 30 to 70 hours with batch fermentation. Increasing the yeast content, as is the case with cell recycle, can considerably reduce the time required for completion of the fermentation. For example, with a cell density of 800 to 1000 million cells per ml, it is possible to reduce the fermentation time to 4 to 10 hours.

Processes for the continuous fermentation of sugars to provide alcohol are also well known (U.S. Pat. Nos. 2,155,134; 2,371,208; 2,967,107; 3,015,612; 3,078,166; 3,093,548; 3,177,005; 3,201,328; 3,207,605; 3,207,606; 3,219,319; 3,234,026; 3,413,124; 3,528,887; 3,575,813; 3,591,454; 3,705,841; 3,737,323; and 3,940,492 "Process Design and Economic Studies of Alternative Fermentation Methods for the Production of Ethanol", Cysewski, et al. Biotechnology and Bioengineering, Vol. xx, pp. 1421-1444 (1978)). In a typical continuous fermentation process, a stream of sterile sugar liquor and a quantity of yeast cells are introduced into the first of a battery of fermentation vessels wherein initial fermentation takes place, generally under conditions favoring rapid cell growth. The partial fermentate admixed with yeast cells is continuously withdrawn from the first fermentation vessel wherein fermentation is carried out under conditions favoring the rapid conversion of sugar to ethanol. The yeast in the last fermentation vessel can be recovered by suitable means, e.g., centrifugation or settlement, and recycled. In such a system, the ability of the fermentation organism to produce ethanol is affected by the ethanol and sugar concentrations. As a rule, a yeast which gives high conversion rates of sugar to ethanol in a low-ethanol, high-sugar fermentation medium will only sluggishly produce ethanol under the opposite conditions, i.e., at high-ethanol level, low-sugar concentrations.

In general, however, the price of bioethanol has not been competitive with that of traditional fossil fuels and it is therefore highly needed to reduce production costs as far as possible by optimizing or improving upon bioethanol production technologies.

SUMMARY OF THE INVENTION

The present invention is directed to an anaerobic fermentation process to enhance or improve ethanol yield, and decrease fermentation time. A process is disclosed using a fermentation broth containing bicarbonate ions for the enhanced production of ethanol from a carbohydrate or sugar containing source. The process for producing ethanol by anaerobic fermentation comprises converting a carbohydrate or sugar source to ethanol using an ethanol producing microorganism in a fermentation broth, wherein said fermentation broth contains one or more carbohydrate or sugar sources, a nitrogen source, bicarbonate ions from a source of bicarbonate ions and water, whereby said ethanol production is enhanced.

In another embodiment, a fermentation broth containing bicarbonate ions is used to increase or enhance ethanol production from the fermentation of an ethanol producing microorganism. A fermentation broth for the fermentation of ethanol from a carbohydrate or sugar source can comprise an ethanol producing microorganism, one or more carbohydrate or sugar sources, a nitrogen source, bicarbonate ions from a source of bicarbonate ions and water.

The present invention provides a viable commercial method for ethanol production and can be used in, for example, fuel ethanol, industrial, cheese, brewing, and wine making industries.

DETAILED DESCRIPTION OF THE INVENTION

The present invention relates to a process for the production of ethanol by anaerobic fermentation. In particular it relates to the production of ethanol by a process of fermentation, in which there is improved or enhanced fermentation efficiency and improved or enhanced yield of ethanol as compared to prior art methods. Ethanol is commonly prepared by the fermentation of carbohydrates and/or sugars or other biological feedstocks. In the fermentation process, the fermentable materials, including an ethanol producing microorganism, are typically added to a large tank where fermentation is accomplished in a batch or continuous process. During fermentation the ethanol producing microorganism cells consume the biomass feedstock in the tank and convert the feedstock to ethanol as they grow. It is well known that yeast cultures metabolize glucose to end products ethanol and carbon dioxide under anaerobic conditions. In this process, glucose is fermented to pyruvate and $CO_2$ by the Embden-Meyerof-Parnis pathway. Pyruvate is then decarboxylated to acetaldehyde via pyruvate decarboxylase, which is then converted into ethanol by alcohol dehydrogenase.

The present invention relates to the enhanced conversion of a carbohydrate or sugar containing source to ethanol and $CO_2$ with ethanol producing microorganism cultures stimulated with bicarbonate ions. As used herein "enhanced conversion" or "increased ethanol production" means enhancing or increasing ethanol production by a fermentation process using an ethanol producing microorganism, in accordance with the present invention, such that ethanol production is enhanced or increased at least 10%, at least 25% or at least 50%, compared to fermentation without bicarbonate ions. In another embodiment, ethanol production can be enhanced or increased up to about 100%, up to about 200%, or up to about 300%, compared to fermentation without bicarbonate ions. In yet another embodiment, the fermentation process is enhanced in the sense that the time required for ethanol producing microorganisms to convert carbohydrates and/or sugars to end products (i.e., ethanol) is reduced or occurs at a faster rate per unit of ethanol producing microorganism.

Typically, the fermentation can be carried out by any known means in the art. For example, the fermentation can be carried out in a continuous process or a batch mode. In accordance with one embodiment of the present invention there is provided a process for the enhanced production of ethanol by fermentation of a carbohydrate or sugar containing source, for example, comprising: (a) crushing or pulping said carbohydrate or sugar containing source to produce a pulp containing substantially no free liquid and comprising particles of said material having diameters of the range up to about 10 mm; (b) where necessary saccharifying and, if desired, heating said pulp to convert non-sugar carbohydrates in said material to sugars; (c) mixing a suspension of ethanol producing microorganism with said pulp (simultaneously with or subsequent to said saccharification, if used) and maintaining said mixture under fermentation conditions to allow said yeast to convert sugars in said pulp to ethanol; and (d) extracting ethanol from said fermented pulp by known means in the art.

The steps of liquefaction, saccharification, fermentation and recovering ethanol are well known. For example these steps are described in Fundamentals of Biotechnology edited by P. Prave, U. Faust, W. Sittig, D. A. Sukatsch, 1987, chapter 10, pages 381-403, incorporated herein by reference. The saccharification and the fermentation steps can be carried out either simultaneously or separately. Preferably the saccharification and the fermentation steps are carried out simultaneously.

Fermentation process parameters are well-known in the art. For example, fermentation can be carried out for about 24 to 96 hours, such as typically for about 35 to 60 hours. In one embodiment, the temperature is generally between 26° and 45° C., in particular from about 30° to about 40° C., and the pH is generally from pH 3 to 8, preferably around pH 4 to 5. The ethanol producing microorganism cells are preferably applied in amounts of $10^5$ to $10^{12}$, preferably from $10^7$ to $10^{10}$, especially $5 \times 10^7$ viable cell count per mL of fermentation broth. During the ethanol producing phase the cell count should preferably be in the range from $10^7$ to $10^{10}$, especially around $2 \times 10^8$. Further guidance in respect of using yeast for fermentation can be found in, e.g., "The alcohol Textbook" (Editors K. Jacques, T. P. Lyons and D. R. Kelsall, Nottingham University Press, United Kingdom 1999), which is hereby incorporated by reference. In a continuous fermentation process, the fermenting mash will be allowed to flow, or cascade, through several fermentors until the mash is fully fermented and then leaves the final tank. In a batch fermentation process, the mash stays in one fermentor for an effective amount of time, for example, for about 48 hours, before distillation is started.

It has surprisingly been found that the addition of bicarbonate ions to the fermentation broth or growth media can act to stimulate and enhance the conversion of a carbohydrate and/or sugar containing sources (e.g., glucose) to ethanol. Not wishing to be bound by theory, it is believed that low levels of bicarbonate ion trigger a controlled optimum pH environment, which allows the yeast cells to reproduce more efficiently and effectively consume the glucose. Other mechanisms may be in play as well which may include: 1) low levels of bicarbonate salt alter membrane permeability or transport proteins, allowing more glucose into the cell and therefore more ethanol production; 2) low levels of bicarbonate salt may reduce protons on the exterior of the mitochondria in the yeast cell, stimulating processes that seek to maintain this gradient, which is important for cell energy generation (these processes would enhance glucose metabolism resulting in higher ethanol production); 3) low levels of sodium bicarbonate salt increase the pH environment around and in the cell, stimulating enzyme activity resulting in increased ethanol production. Experimentation has shown that higher pH levels around the yeast cells did occur with addition of bicarbonate (pH 7.5), but increased ethanol production also occurred when the pH around the cell was lower (4.5).

Typically, the bicarbonate ion source can be any known source of bicarbonate ions. For example, the bicarbonate source is typically an alkali metal or magnesium bicarbonate, more preferably sodium, potassium or ammonium bicarbonate, most preferably, sodium bicarbonate. A bicarbonate concentration of from about 100 ppm to about 2000 ppm, relative to the fermentation broth, can be used to stimulate or enhance fermentation of a carbohydrate or sugar containing source to ethanol, in accordance with the present invention. A bicarbonate concentration of from about 200 ppm to about 1000 ppm, or from about 200 to about 500 ppm, relative to the fermentation broth, may also be useful for the enhanced production of ethanol. However, it is also well known that sodium bicarbonates, potassium bicarbonate and ammonium bicarbonate can have adverse metabolic effects on ethanol producing microorganisms. The bicarbonate salts at high concentrations (typically greater than 10,000 ppm relative to the fermentation broth) can act as natural fungicides or mildewcides; retarding or killing these organisms. The difference between stimulating cell cultures and retarding cell cultures is dependent on the concentration of bicarbonate. At high concentrations, bicarbonates: 1) interacts with membrane to alter normal membrane activities and disrupt cellular physiology; 2) interactive extra-cellular enzymes; 3) raise the pH, which affects cellular activity of cell membranes, and affects electron transport; and 4) causes an osmotic effect (may dehydrate cell). Typically, bicarbonate concentrations of 10,000 ppm and higher can have fungistatic or fundicidal and mildewstatic or mildewcidal effects, and thus, should be avoided.

As used herein, the terms "nutrient medium," "fermentation broth" and "growth media" are used interchangeably. These terms refer to both (i) media in the form originally provided to the ethanol producing microorganism as a source of nutrient and (ii) media produced after some or all of the originally provided nutrients have been consumed and fermentation products including ethanol have been excreted into the media by the microorganism. The "fermentation broth" of the present invention comprises a water based composition including minerals and their salts necessary for growth of the ethanol producing microorganism of the present invention. The fermentation broth of the present invention typically contains an ethanol producing microorganisms (e.g., yeast), effective amounts of a carbon source (i.e., carbohydrate and/or sugar containing sources), a nitrogen source, optionally a phosphate source, optionally a sulfate source, optionally a calcium source and optionally trace elements, such as vitamins and minerals sufficient to permit growth and ethanol production. The fermentation broth of the present invention is typically maintained at a pH and temperature to influence rate of fermentation to form ethanol. Additional factors within the broth that may also effect rate of fermentation are concentration of carbohydrates and/or sugars, activity of microorganisms and enzymes.

The ethanol producing microorganism of the present invention typically can utilize a number of carbon and energy sources for growth and/or ethanol production, including carbohydrate and/or sugar containing sources. For example, the ethanol producing microorganism of the present invention may be able to utilize glucose, fructose, galactose, melibiose, sucrose, raffinose, and/or stachyose as a carbon or energy source. Some of the ethanol producing microorganisms may be able to use all or most of these sugars as a source of carbon and energy while other strains are more fastidious and may only be able to grow on one or two sugars from the list. In other instances, a starch (such corn starch) or a hydrolysate thereof may be used as primary carbohydrate source.

It has been found that suitable fermentation broths for use in the present process preferably include at least about 20 g/L, at least about 30 g/L, at least about 40 g/L of one or more carbohydrate and/or sugar containing sources. More preferably, the fermentation broth includes at least about 70 g/L and, most preferably, at least about 100 g/L of the carbohydrate and/or sugar containing sources. The carbohydrate or sugar containing source is typically made up of glucose, fructose, galactose, melibiose, sucrose, raffinose, stachyose, or a mixture thereof. Glucose, fructose, and sucrose are particularly suitable for use as a carbon and energy source in the fermentation broth.

A nitrogen providing compound is also provided in the fermentation broth of the present invention to provide an initial nitrogen source for the ethanol producing microorganism to begin growth and start the fermentation process. Nitrogen producing compounds may include ammonium phosphate, urea or any other suitable compound containing nitrogen. The nitrogen producing compound may be present by weight in an amount of between about 0.1% and 10%, and more preferably between about 0.15% and 5%, and most preferably between about 0.18% and 3%.

As one of skill in the art will appreciate, the fermentation process, and thus, ethanol production can be optimized by using optimal concentrations of the carbon and nitrogen sources in the fermentation broth so that the maximum possible specific product formation rate can be maintained for extended periods. In this way, the process yield and productivity can be improved or optimized for a process or a phase of the process and the batch-to-batch consistency can be improved. This general approach applies for any process, whether the product is a primary metabolite, a secondary metabolite, or the biomass itself.

Typically, any microorganism capable of converting a carbohydrate or sugar containing source (e.g., glucose) to ethanol can be used in the fermentation process of the present invention. For example, a suitable microorganism may include a fungi strain, such as yeast or mold. This fungal strain may include a mesophilic microorganism (i.e. one which grows optimally at a temperature in the range of 20-40° C.), e.g. a yeast also referred to as "baker's yeast", Saccharomyces cerevisiae.

The microorganisms used in the fermentation process of the present invention can be any microorganism capable of converting a carbohydrate or sugar containing source (e.g., glucose) to ethanol. For example, a yeast such as Klyveromyces species, Candida species, Pichia species, Brettanomyces species, Saccharomyces species such as Saccharomyces cerevisiae and Saccharomyces uvarum, Hansenula species and Pachysolen species.

In the fermentation step, yeast can be added to the mash or to the fermentation broth to ferment sugars to ethanol and carbon dioxide. Preferred yeast includes strains of the genus Saccharomyces, more preferably, strains of Saccharomyces cerevisiae. Commercially available yeast include, e.g. RED STAR®/LESAFFRE ETHANOL RED (available from Red Star/Lesaffre, USA), SUPERSTART™ (available from Alltech), GERT STRAND (available from Gert Strand AB, Sweden) and FERMOIL (available from DSM specialties).

It will be appreciated by one of skill in the art, that a useful ethanol producing microorganism can also be selected from a genetically modified organism of one of the above useful organisms having, relative to the organism from which it is derived, an increased or improved ethanol-fermenting activity.

Regardless of the source of fermentable carbohydrate or sugar, the fermentation step itself may be characterized by end-product inhibition. The conversion of sugar to ethanol may cease when the volume concentration of ethanol becomes toxic to the fermenting organism. This often occurs when a concentration of greater than about 10%, greater than about 12%, or greater than about 15% by volume ethanol is reached. Thus, in one embodiment, it may be useful to recover or remove ethanol from the fermentation broth by known methods in the art.

Fermentation reaction vessels (fermentors) of any suitable, known type may be employed in performing the fermentation process of the present invention. For further details of suitable reaction vessels, reference may be made, for example, to J. E. Bailey and D. F. Ollis, 1986. Batch fermentation and continuous fermentation are both suited in this connection.

A variety of reactor configurations including packed bed reactors, continous stirred tank reactors, rotating biological contact reactors, sequencing batch reactors and fluidized bed reactors may be employed in the present process. The entire reaction may be performed in a single vessel having appropriate means to control the temperature of the fermentation broth or, alternatively fermentation may be carried out in a first vessel, the broth may be maintained at the desired temperature by passage through a heat exchanger, for example, a plate heat exchanger and recycled to the fermentation reaction. The latter arrangement can provide more rapid cooling of the reaction mixture and can in some instances be carried out at the same time that broth is passed through a membrane separation module to remove a portion of the broth (e.g., where the heat exchanger and membrane module are connected in series).

Another general approach to fermentation process control is the use of continuous processes. Growth and metabolism are easily controllable in continuous bioreactors such as the chemostat, the pH-stat, and the RAR-stat. The latter was disclosed by H. Shimamatsu et al., "Process for Continuous Cultivation of Protein-Producing Microorganisms," U.S. Pat. No. 4,021,304 (May 3, 1977) and shown by P. Agrawal, "An Experimental Study of Acid Production Rate Controlled Operations of a Continuous Fermentor," Bioprocess Eng., Vol. 4, pp. 183-190 (1989), and is also referred to as an APR-stat (acid production rate). In continuous processes, the volume is constant because fresh medium is added at the same rate that broth (medium plus biomass) is withdrawn. This leads to a steady state with respect to substrate, nutrient, biomass, and product concentrations, and thus a controlled growth and metabolism, is easily attainable. Growth and metabolism are controlled through the substrate and nutrient concentrations in the fresh medium and through the dilution rate for the chemostat, the buffering capacity of the fresh medium for the pH-stat, or the RAR set point for the RAR-stat (in all continuous processes, the growth rate equals the dilution rate at steady state). However, continuous fermentors are generally not used by industry because of various practical concerns such as the increased risk of contamination and the desire for batch downstream processing. Instead, fed-batch fermentors are preferred even though steady state is much harder to reach because of the lack of convection (in fed-batch reactors, the dilution rate is much less than the growth rate because concentrated feeds are used to minimize the increase in the volume).

The present fermentation process may be run in a continuous fashion where a fraction of the fermentation broth is removed as the fermentation proceeds. This may be done either continuously or at periodic intervals. Sufficient fermentation broth is typically added to the reactor to maintain a constant liquid volume. Under such fermentation conditions, steady state conditions (in terms of pH, glucose concentration and nutrient concentrations) are generally achieved and maintained after an initial startup phase has been concluded. When fermentation is conducted in this manner, the average incubation pH (the pH during the startup phase is ignored) and the final incubation pH of the broth are essentially the same.

EXAMPLE

Experimental Protocol:

Various concentrations of yeast were added to glucose based liquid media with and without $NaHCO_3$ and the fermentation process monitored for glucose consumption and ethanol production.

The fermentation media consisted of 25 gm of glucose and 1 ml of urea (45%) in 250 ml of water. The pH of the system was adjusted to 4.5 with 1 M $H_2SO_4$. The temperature of incubation was about 32° C., and the tests were conducted for 72 hours. The tests compared fermentation systems with and without sodium bicarbonate ($NaHCO_3$). $NaHCO_3$ was added to final concentrations of 200 ppm or 500 ppm in the test vessels. The pH after NaHCO3 addition was about 7.5. In some vessels the pH was readjusted to 4.5. Yeasts (*Saccharomyces cerevisiae* (Ethanol Red) diluted 1 to 5 in water, were added to the various test vessels at 0.5, 2, 3, 4 and 5 ml. Yeasts at 3 ml in the vessel corresponds to 2.4 g/L. The fermentation media vessels were monitored for glucose utilization and ethanol production via HPLC measurement at 2, 4, 6, 24, 48 and 72 hours.

From the Figure it can be seen that $NaHCO_3$ affected ethanol production by increasing rate of yeast fermentation.

$NaHCO_3$ increased ethanol production by stimulating yeast fermentation. Yeasts (3 ml) with $NaHCO_3$ showed the best rate of ethanol production (seen at times 24 and 48 h). Ethanol production may have been restricted for higher yeast concentrations because glucose was limiting.

Summary of Results:

We have found the following beneficial effects of bicarbonate on yeast conversion of glucose to ethanol:

| | Glucose concentration at 10% | | |
|---|---|---|---|
| SBC | 0 | 200 ppm | 500 ppm |
| Yeast (g/L) | 2.4 | 2.4 | 2.4 |
| Ethanol (% after 48 hours) | 2.4 | 4.8 | 4.8 |

What is claimed is:

1. A fermentation broth for the fermentation of ethanol from a carbohydrate or sugar source comprising: an ethanol producing microorganism, one or more carbohydrate or sugar sources, a nitrogen source, bicarbonate ions from a source of bicarbonate ions, and water; wherein said bicarbonate ions are added to provide a concentration of from 200 to 500 ppm relative to said fermentation broth, and wherein the pH value of said fermentation broth is subsequently adjusted to between 4 and 5.

2. The fermentation broth of claim 1, wherein said source of bicarbonate ions is selected from the group consisting of sodium bicarbonate, potassium bicarbonate and ammonium bicarbonate.

3. The fermentation broth of claim 1, wherein said ethanol producing microorganism is yeast.

4. The fermentation broth of claim 3, wherein said yeast is selected from the group consisting of a *Klyveromyces* species, *Candida* species, *Pichia* species, *Brettanomyces* species, *Saccharomyces* species selected from *Saccharomyces cerevisiae* and *Saccharomyces uvarum*, *Hansenula* species and *Pachysolen* species.

5. The fermentation broth of claim 3, wherein said yeast is *Saccharomyces cerevisiae*.

* * * * *